United States Patent

Sumiya

Patent Number: 5,549,599
Date of Patent: Aug. 27, 1996

[54] APPARATUS FOR LASER SURGERY ON A CORNEA

[75] Inventor: Toshifumi Sumiya, Nukata-gun, Japan

[73] Assignee: Nidek Co., Ltd., Aichi, Japan

[21] Appl. No.: 415,213

[22] Filed: Apr. 3, 1995

[30] Foreign Application Priority Data

Apr. 28, 1994 [JP] Japan ................................ 6-114442

[51] Int. Cl.$^6$ .................................................. H61N 5/06
[52] U.S. Cl. .............................. 606/10; 606/5; 606/12; 606/13
[58] Field of Search ....................... 606/2, 3–18

[56] References Cited

U.S. PATENT DOCUMENTS

| | | | |
|---|---|---|---|
| 4,669,466 | 6/1987 | L'Esperance | 606/3 |
| 4,913,142 | 4/1990 | Kittrell et al. | 606/15 |
| 4,988,348 | 1/1991 | Bille | 606/5 |

FOREIGN PATENT DOCUMENTS

| | | | |
|---|---|---|---|
| 207648 | 1/1987 | European Pat. Off. | 606/3 |

Primary Examiner—David M. Shay
Attorney, Agent, or Firm—Rossi & Associates

[57] ABSTRACT

An apparatus for laser surgery on a cornea for correcting the refractive error of a patient's eye by removing away a part of the cornea by a laser beam. The apparatus has a first set device for setting the removing area in removal of stroma of the cornea, a second set device for setting the shape of the postoperation cornea, a device for restricting laser irradiation to the removing area determined by the second set device, a device for detecting whether removal of the epithelium from the cornea is accomplished, a device for changing a mode to remove away the epithelium to a mode to remove the stroma of the cornea based on detected results by the detecting device, and a control device for determining the area to be removed away on the epithelium based on the removing area set by the first set device in a mode for removing the epithelium of the cornea and driving the beam restricting device, and then for controlling the beam restricting device based on the set data by the second set device in a mode for removing the stroma of the cornea, thereby to remove away the stroma from the cornea in a desired shape.

11 Claims, 3 Drawing Sheets

APPARATUS FOR LASER SURGERY ON A CORNEA

BACKGROUND OF THE INVENTION

1. Field of the Invention

The present invention relates to an apparatus for laser surgery on a cornea, in which a laser beam ablates away a surface of a cornea to correct the refractive error of an eye.

2. Description of Related Art

There is a known method for correcting the refractive error of an eyeball by removing away stroma underlying epithelium of the cornea in a lens-like shape by a laser beam to change its curvature. This can be called Photorefractive Keratectomy. In a conventional surgery method, the epithelium constituting the anterior surface of the cornea would be peeled off in advance of irradiation of a laser beam thereto. This peeling method of the epithelium from the cornea was a mechanical method using a hockey knife and the like to scrape the epithelium.

In such a mechanical removing method with a hockey knife and the like, the time needed for removing the epithelium of the cornea would differ from operator to operator according to each skill and others, this influencing the dry condition of the stroma of the cornea and causing a change of the moisture content of the stroma. Accordingly, there occurs a problem that, if an excimer laser beam which is high absorbable into water is used for ablating the stroma of a cornea, change of a dry condition of the stroma causes large variations in ablation depths on the stroma. As a result, the actual ablated shape of the stroma of the cornea differs from a predetermined shape of the stroma, resulting in errors in the corrected refractive power of the postoperation cornea.

SUMMARY OF THE INVENTION

The present invention has been made in view of the above circumstances and has an object to overcome the above problems and to provide an apparatus for laser surgery on a cornea, capable of minimizing variations in the dry condition of the stroma during removing of the epithelium from a cornea and of obtaining stable results postoperation as intended in preoperation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an apparatus for laser surgery on a cornea for correcting the refractive error of a patient's eye by removing away a part of the cornea by a laser beam of this invention, the apparatus comprising the first set means for setting the removing area in removal of stroma of the cornea, the second set means for setting the shape of the postoperation cornea, means for restricting laser irradiation to the removing area determined by the second set means, means for detecting whether removal of the epithelium from the cornea is accomplished, means for changing a mode to remove away the epithelium to a mode to remove the stroma of the cornea based on detected results by the detecting means, and control means for determining the area to be removed away on the epithelium based on the removing area set by the first set means in a mode for removing the epithelium of the cornea and driving the beam restricting means, and then for controlling the beam restricting means based on the set data by the second set means in a mode for removing the stroma of the cornea, thereby to remove away the stroma from the cornea in a desired shape.

According to the present invention, after removing away the epithelium of the cornea by a laser beam, the apparatus is capable of promptly shifting to the laser ablation on the stroma of the cornea, so that variations in dry conditions of the stroma in removing of the epithelium can be reduced and thus stable operation results can be obtained.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

DETAILED DESCRIPTION OF THE PREFERRED EMBODIMENTS

A detailed description of some preferred embodiments of an apparatus for laser surgery on a cornea embodying the present invention will now be given referring to the accompanying drawings.

Figure 1:
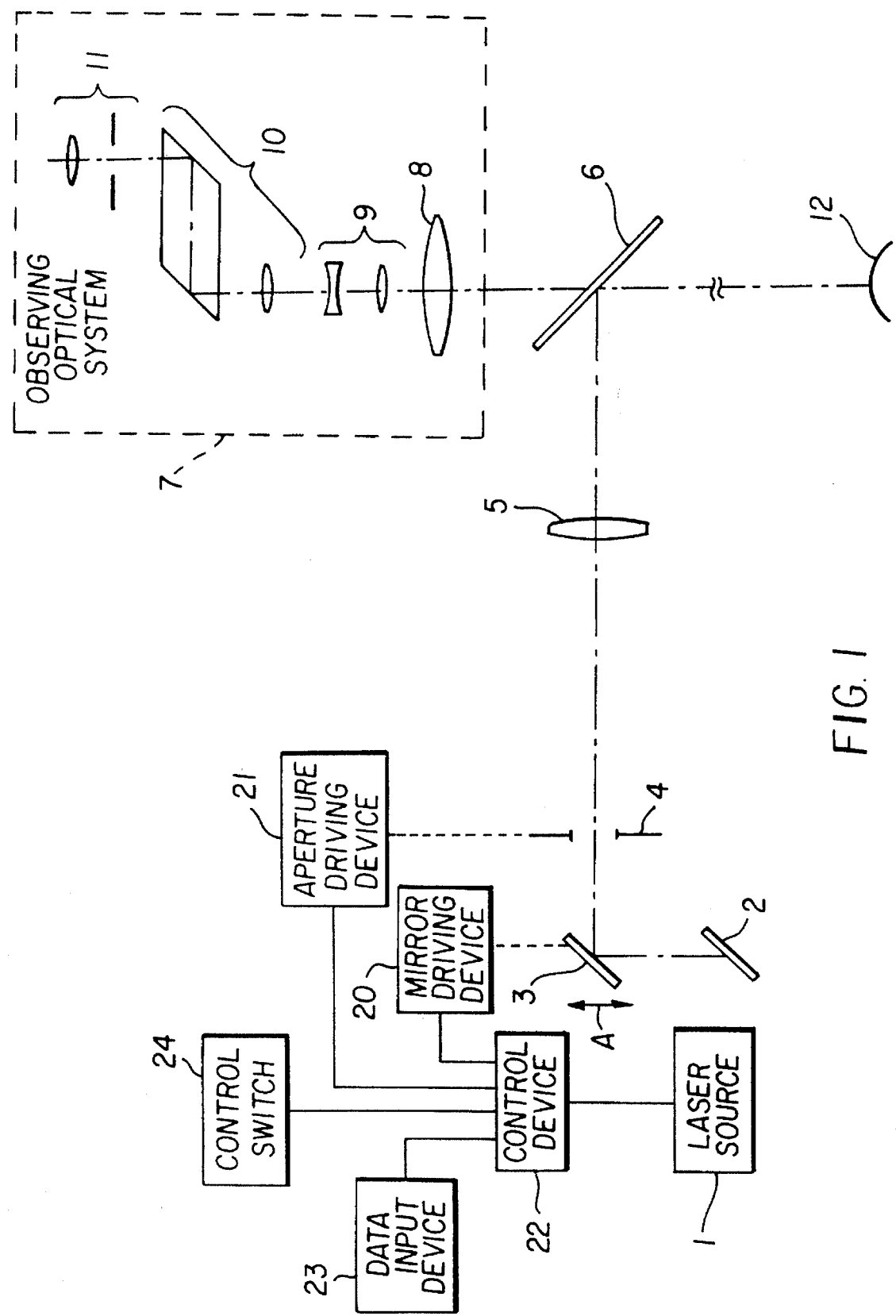
FIG. 1 is a schematic diagram of an arrangement of an optical system and a control system in an apparatus of the first embodiment according to the present invention.

FIG. 1 shows a schematic arrangement of an optical system and a control system of the apparatus in the first embodiment.

Figure 2:
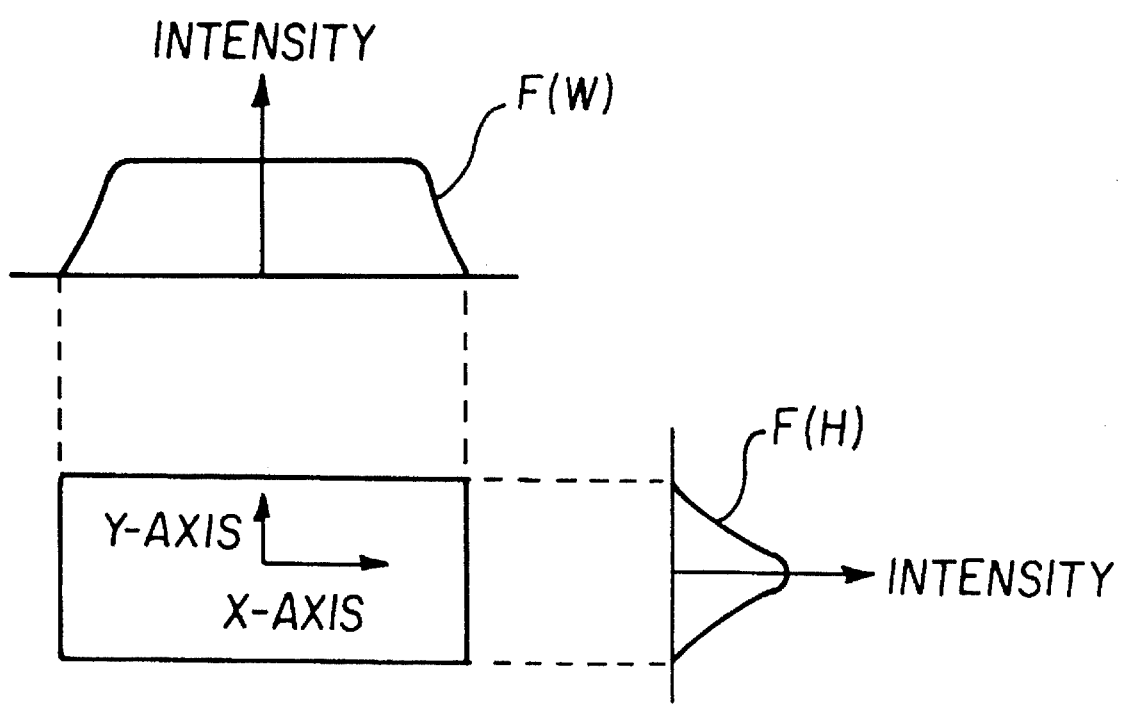
FIG. 2 is a schematic diagram of a typical shape of an excimer laser beam.

Numeral 1 is a laser source which preferably uses an excimer laser having a wavelength of 193 nm in the present embodiment. The standard shape of the excimer laser beam emitted from the laser source 1 has a beam profile schematically shown in FIG. 2, which has an almost uniform density distribution indicated by F(W) of the laser beam in a horizontal direction, i.e., x-axis direction and a gaussian distribution indicated by F(H) in a vertical direction, i.e., y-axis direction.

Plane mirror 2 serves for reflecting the laser beam emitted from the laser source 1 at right angle upward and plane mirror 3 serves for subsequently reflecting the laser beam in a horizontal direction toward an aperture diaphragm 4 mentioned later. The plane mirror 3 is movable in a direction indicated by an arrow A by a mirror driving device 20, thereby making the laser beam scan the object in the gaussian distribution F(H) direction, i.e., the y-axis direction in FIG. 2, so that the object is ablated in a uniform depth. This laser ablation by scanning has been described in detail in U.S. application Ser. No. 08/187,124 which is based on Japanese Patent Application No. 2-41676, please see it for understanding thereof.

Aperture diaphragm 4, disposed on an optical path of the laser beam, serves for restricting the ablation area on the cornea 12 of patient's eye, aperture diameter of which is changeable by an aperture driving device 21. Numeral 5 is a projective lens to project an image of the aperture diaphragm 4 onto the cornea 12. The aperture diaphragm 4 is disposed in a position substantially conjugate with the cornea 12 with respect to the projective lens 5.

The laser beam passed through the aperture diaphragm 4 forms an image of the aperture diaphragm 4 by the projective lens 5 on the cornea 12, restricting the ablation area.

Numeral 6 is a dichroic mirror serves for reflecting the laser beam passed through the projective lens 5 so as to be coaxial with the optical path of an observing optical system.

The apparatus is also provided with a binocular surgical microscope having an observing optical system 7. This observing optical system 7 is constructed of the objective lens 8, a group of variable power lenses 9, binocular parts 10 and eyepieces 11, in which these optical components 9–11 except for the objective lens 8 are constituted in a pair respectively for right and left eyes.

The position of the cornea 12 of the eye to be operated is determined in advance so as to have a predetermined positional relationship with the apparatus. Hardly relating to the present invention, the positioning means is not illustrated in particular in the present embodiment.

The control system of the apparatus has a control device 22 for controlling all of the apparatus, a data input device 23 by which data of the refractive power of the eye to be operated and the like are input to the control device 22 and a control switch part 24 provided with a mode changing switch for changing a mode to remove the epithelium of the cornea to another mode to remove the stroma of the cornea, and the like.

While using the apparatus constructed as above, surgical operation from removal of the epithelium of the cornea until correction of the refractive power will be described hereinafter.

The operator first determines the ablation area on the stroma of the cornea of patient's eye and the ablation depth, and inputs such data in advance into the data input device 23. Subsequently, patient's eye is disposed at a predetermined position with respect to the apparatus by means of a positioning means not illustrated in the present embodiment. The mode changing switch of the control switch part 24 is set to select a mode to remove the epithelium of the cornea. When the epithelium removing mode is selected, the control device 22 drives the aperture driving device 21 to set an aperture diameter of the aperture diaphragm 4 so as to cover the ablation area. This aperture diameter of the aperture diaphragm 4 is determined so as to be slightly wider size than the ablation area.

The operator then depresses a laser irradiation switch of the control switch part 24 to irradiate and ablate the cornea 12 by a laser beam. When the laser beam starts to ablate the epithelium of the cornea 12, the epithelium generates fluorescence by optical effect produced between the laser beam and the tissue component of the epithelium. The operator can view the fluorescence generated from the epithelium through the observing optical system 7.

While irradiating the laser beam to the cornea 12, the epithelium is removed away from the cornea and the stroma underlying the epithelium is succeedingly ablated. When the laser beam starts to ablate the stroma of the cornea, fluorescence generated from the stroma will vary its color from that of the epithelium in ablating owing to the difference between each tissue component of the epithelium and the stroma of the cornea. The operator can views this color variation in fluorescence through the observing optical system 7, finding a completion of removal of the epithelium.

When confirming the color variation in fluorescence generated from the cornea 12, the operator changes a mode switch of the control switch part 24 to change into a mode to remove the stroma of the cornea. On receiving a switch signal from the control switch part 24, the control device 22 drives the aperture driving device 21 to vary in turn the aperture diameter of the aperture diaphragm 4 while ablating the cornea by the laser beam, so that the curvature of the stroma of the cornea is changed to a desired curvature. At this time, each aperture diameter of the aperture diaphragm 4 to be changed is determined based on data including the desired refractive power after correction and the ablation area and the like that are input in advance to the apparatus. In such a way, correcting the refractive power of the cornea is accomplished.

Next, the second embodiment according to the present invention will be described hereinafter.

In the first embodiment, as described above, to change a mode for removing the epithelium to another mode for removing the stroma, the operator manually operates a mode changing switch while observing color variations in the fluorescence caused by laser irradiation. In the second embodiment, the apparatus is further provided with a detecting optical system to detect the color variation in the fluorescence and constructed so that a mode be automatically changed to another based on results by the detecting optical system, from one for removing the epithelium to another for removing the stroma of the cornea.

Figure 3:
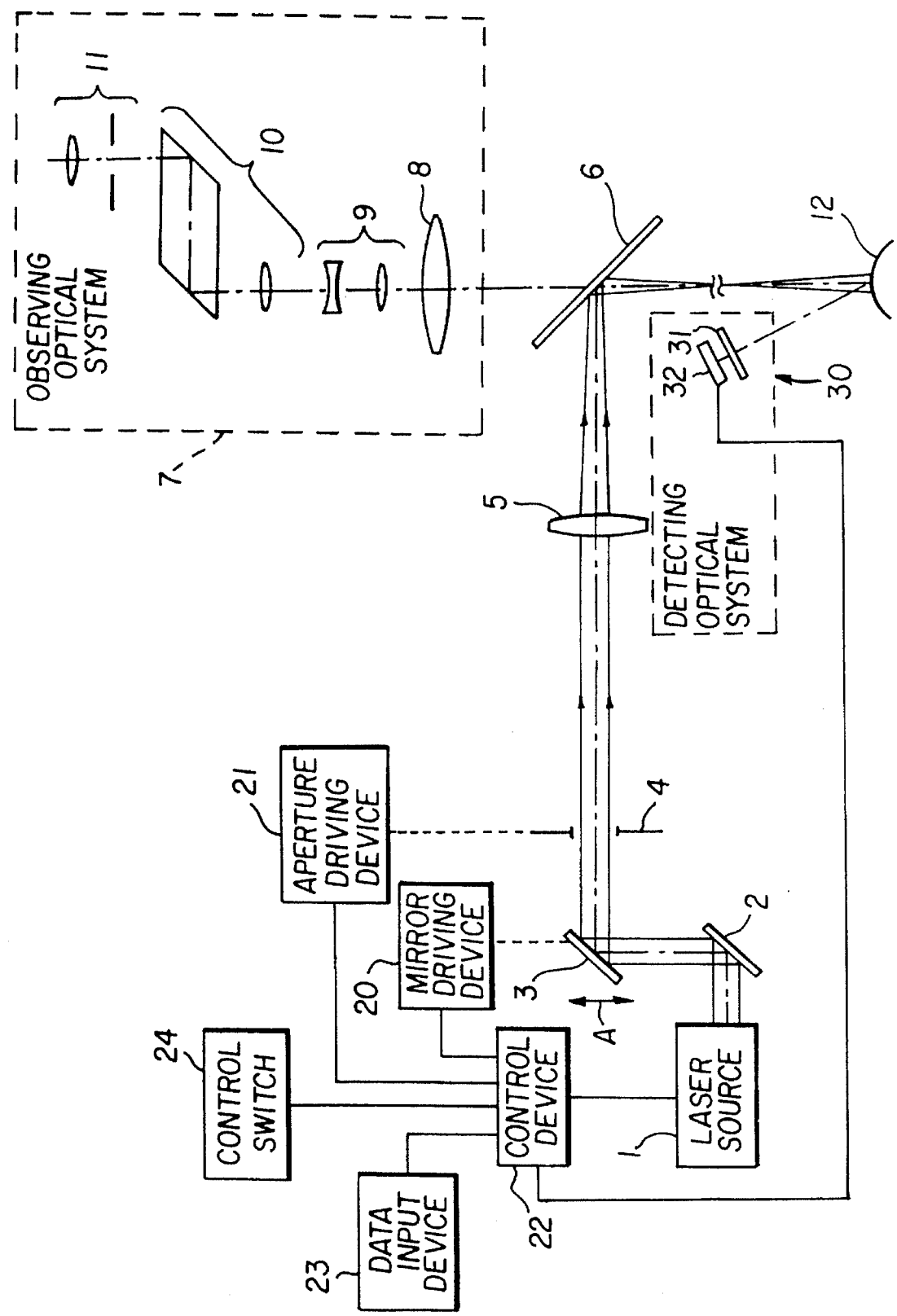
FIG. 3 is a schematic diagram of an arrangement of an optical system and a control system in an apparatus of the second embodiment according to the present invention.

FIG. 3 shows a schematic arrangement of the optical system and the control system of the apparatus in the second embodiment, in which similar components as in the first embodiment are labeled with the same numbers and each description is omitted accordingly.

Numeral 30 is the detecting optical system for detecting fluorescence emitted from the cornea 12 during the ablation, which is provided with a filter 31 and a photodetector 32. This detecting optical system 30 is movable integrally with the apparatus body and thus aligned along with the apparatus by the positioning means. The filter 31 has spectral characteristics of cutting a wavelength of the fluorescence generated from the epithelium and, to the contrary, of transmitting a wavelength of the fluorescence generated from the stroma during the excimer laser irradiation. The detecting optical system 30 may also be provided with a condensing lens. Though the present embodiment does not use a detecting optical path in common with observing and laser irradiating optical paths, it may use partially those optical paths in common by diverging a detecting optical path from an observing optical path and others.

In the above constructed apparatus in the second embodiment, the wavelength of the fluorescence is changed into a wavelength capable of transmitting through the filter 31 according to a change of the ablated region of the cornea from the epithelium to the stroma, so that the output from the photodetector 32 increases accordingly. The output signal from the photodetector 32 is then input to the control device 22. The control device 22 detects the ablation region is shifted from the epithelium to the stroma based on the input signal and change automatically a mode to correct the refractive power of the eye while varying in turn the aperture diameter of the aperture diaphragm 4.

It is also possible to use a filter, contrary to the above filter 31, having optical characteristics of transmitting a wavelength of the fluorescence generated from the epithelium and of cutting the same from the stroma, then the output from the photodetector 32 merely becoming contrary.

Although proposed are methods to limit an area to be irradiated such that scanning a laser beam while restricting it into a spot form, the present invention can be used in any apparatus.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for laser surgery on a cornea for correcting the refractive error of a patient's eye by removing a part of the cornea by a laser beam, the apparatus comprising:

a first set means for setting a stroma removing area of the cornea;

a second set means for determining an amount of removal in said removing area of the cornea by determining a corneal shape after surgery based on the removing area and the amount of a refracting correction;

restricting means for restricting laser irradiation to a desired removing area of the cornea;

detecting means for detecting a change of fluorescent light generated from irradiated cornea tissue;

control means for controlling said restricting means in first and second modes, the first mode irradiating a laser beam to an epithelium of the cornea to be removed based on the removing area set by said first set means, and the second mode irradiating the laser beam to the stroma according to said second set means; and mode changing means in communication with said control means for changing the first mode to the second mode based on the change of fluorescent light detected by said detecting means.

2. An apparatus for laser surgery on a cornea according to claim 1, wherein said detecting means is provided with an observing optical system for observing the cornea, through which color variations in fluorescence generated from tissue of the cornea by laser irradiation may be observed.

3. An apparatus for laser surgery on a cornea according to claim 1, wherein said detecting means includes a photodetector for detecting color variations in fluorescence that tissue of the cornea generates by laser irradiation, and said mode changing means is driven based on the results detected by the photodetector.

4. An apparatus for laser surgery on a cornea according to claim 3, wherein said detecting means is provided with a filter having characteristics of blocking either a wavelength of fluorescent light generated from the epithelium or the stroma of the cornea when irradiated by the laser beam.

5. An apparatus for laser surgery on a cornea for correcting the refractive error of a patient's eye by removing a part of the cornea by an ultraviolet laser beam, the apparatus comprising:

a laser source for emitting an ultraviolet laser beam;

a light delivery optical system for delivering the ultraviolet laser beam to the cornea of the eye to be operated on;

a first set means for determining a setting for an ablation area of a stroma of the cornea;

a second set means for determining an amount of removal at said ablation area of the cornea by determining a corneal shape after surgery based on the ablation area and the amount of the refracting correction;

restricting means for variably restricting laser irradiation to a desired removing area of the cornea;

an observing optical system for observing color variations in fluorescence generated by tissue of the cornea when irradiated by the ultraviolet laser beam;

control means for controlling said restricting means in first and second modes, the first mode irradiating the laser beam to an epithelium of the cornea to be removed based on the removing area set by said first set means, and the second mode irradiating the laser beam to the stroma according to said second set means; and means in communication with said control means for changing the first mode to the second mode.

6. An apparatus for laser surgery on a cornea according to claim 5, said observing optical system is provided with a mirror having characteristics of transmitting one of the observing light and the ultraviolet laser beam and of reflecting another.

7. An apparatus for laser surgery on a cornea according to claim 5, wherein said restricting means comprises a variable aperture diaphragm disposed on an optical path of the light delivery optical system.

8. An apparatus for laser surgery on a cornea for correcting the refractive error of a patient's eye by removing a part of a cornea by an ultraviolet laser beam, the apparatus comprising:

a laser source for emitting an ultraviolet laser beam;

a light delivery optical system for delivering the ultraviolet laser beam to the cornea of the eye to be operated on;

a first set means for setting a stroma removal area of the cornea;

a second set means for determining an amount of removal in said removal area of the cornea by determining a corneal shape after surgery based on the removal area and the amount of the refracting correction;

restricting means for changeably restricting the ultraviolet laser beam irradiation to a desired removing area of the cornea;

a fluorescent color detecting system for detecting color variations in fluorescence that tissue of the cornea generates by said ultraviolet laser irradiation;

control means for controlling said restricting means in first and second modes, the first mode irradiating the laser beam to an epithelium of the cornea to be removed based on the removal area set by said first set means, and the second mode irradiating the laser beam to the stroma according to said second set means; and means in communication with said control means for changing the first mode to the second mode based on the change of fluorescent light detected by said fluorescent color detecting system.

9. An apparatus for laser surgery on a cornea according to claim 8, wherein said fluorescent color detecting system is provided with a filter having a characteristic of blocking a wavelength of either fluorescence generated from the epithelium or the stroma when irradiated by the ultraviolet laser beam, and a photodetector for detecting the fluorescence transmitted through the filter.

10. An apparatus for laser surgery on a cornea according to claim 8, further comprising an observing optical system for observing the eye to be operated on, said observing optical system being provided with a mirror having characteristics of transmitting one of the observing light and the ultraviolet laser beam and of reflecting another.

11. An apparatus for laser surgery on a cornea according to claim 8, wherein said restricting means comprises a variable aperture diaphragm disposed on an optical path of the light delivery optical system.

* * * * *